US011851396B2

(12) United States Patent
Cenanovic et al.

(10) Patent No.: US 11,851,396 B2
(45) Date of Patent: Dec. 26, 2023

(54) PRESERVATIVE COMPOSITION

(71) Applicant: Aktiebolaget SKF, Gothenburg (SE)

(72) Inventors: Amra Cenanovic, Hisings Backa (SE); Frank Fiddelaers, Gorinchem (NL); Remko Thijssen, Oss (NL); Albert van den Kommer, Nieuwegein (NL); Roel van der Zwaan, Ter Aar (NL)

(73) Assignee: Aktiegolaget SKF, Gothenburg (SE)

( * ) Notice: Subject to any disclaimer, the term of this patent is extended or adjusted under 35 U.S.C. 154(b) by 0 days.

(21) Appl. No.: 17/605,321

(22) PCT Filed: May 7, 2020

(86) PCT No.: PCT/EP2020/062740
§ 371 (c)(1),
(2) Date: Oct. 21, 2021

(87) PCT Pub. No.: WO2020/225372
PCT Pub. Date: Nov. 12, 2020

(65) Prior Publication Data
US 2022/0213403 A1    Jul. 7, 2022

(30) Foreign Application Priority Data
May 7, 2019   (DE) .......................... 102019206560.0

(51) Int. Cl.
*C07C 309/35*   (2006.01)
*C09D 7/63*    (2018.01)
(Continued)

(52) U.S. Cl.
CPC .............. *C07C 309/35* (2013.01); *C09D 7/63* (2018.01); *C09K 15/22* (2013.01); *C10M 133/16* (2013.01);
(Continued)

(58) Field of Classification Search
CPC .......... C07C 309/35; C08K 5/42; C09D 7/63; C09K 15/22; C10M 133/16;
(Continued)

(56) References Cited

U.S. PATENT DOCUMENTS 2,944,021 A * 7/1960 Ulzheimer et al. .. C10M 173/00
508/178
3,179,630 A    4/1965 Endrey
(Continued)

FOREIGN PATENT DOCUMENTS

CN    101084295 A    12/2007
CN    101372643 A    2/2009
(Continued)

OTHER PUBLICATIONS

Database WPI Week 201154 Thomson Scientific, London, GB; AN 2011-J92777 XP002799625, -& CN 102 108 513 A (Pla Anti Chem Command&Eng College) Jun. 29, 2011 (Jun. 29, 2011) abstract paragraph [0012] paragraphs [0050], [0057] examples 1-10 claims.

*Primary Examiner* — James C Goloboy
(74) *Attorney, Agent, or Firm* — GARCIA-ZAMOR INTELLECTUAL PROPERTY LAW, LLC; Ruy Garcia-Zamor

(57) ABSTRACT

The present invention provides a preservative composition to prevent and/or reduce corrosion on a metal surface comprising an anhydride-derived amide and an oil and/or a solvent, wherein the anhydride-derived amide is present in an amount in the range of from 0.01-50 wt %, based on the total weight of the preservative composition. The invention also provides a preservative composition comprising in addition a sulfonate composition; a metal article having a coating thereon which coating comprises the present pre-
(Continued)

servative composition; and the use of the present preservative composition to prevent and/or reduce corrosion on a metal surface.

16 Claims, 2 Drawing Sheets

(51) Int. Cl.
| | |
|---|---|
| *C09K 15/22* | (2006.01) |
| *C10M 133/16* | (2006.01) |
| *C10M 141/08* | (2006.01) |
| *C10M 169/04* | (2006.01) |
| *C08K 5/42* | (2006.01) |
| *C10M 135/10* | (2006.01) |
| *C10N 30/12* | (2006.01) |
| *C10N 40/02* | (2006.01) |

(52) U.S. Cl.
CPC ........ C10M 141/08 (2013.01); C10M 169/04 (2013.01); *C08K 5/42* (2013.01); *C10M 135/10* (2013.01); *C10M 2203/003* (2013.01); *C10M 2215/28* (2013.01); *C10M 2219/044* (2013.01); *C10N 2030/12* (2013.01); *C10N 2040/02* (2013.01)

(58) Field of Classification Search
CPC .............. C10M 135/10; C10M 141/08; C10M 169/04; C10M 2203/003; C10M 2215/28; C10M 2219/044; C10N 2030/12; C10N 2040/02
See application file for complete search history.

(56) References Cited

U.S. PATENT DOCUMENTS

| | | | |
|---|---|---|---|
| 3,567,504 A | 3/1971 | Hopkins et al. | |
| 3,773,479 A * | 11/1973 | Dorn ....................... | C10L 1/224 44/407 |
| 4,108,784 A | 8/1978 | Bryant | |
| 4,479,882 A * | 10/1984 | Zoleski ................ | C10M 145/36 508/460 |
| 4,505,835 A * | 3/1985 | Sung .................... | C10M 133/16 562/561 |
| 6,436,882 B1 * | 8/2002 | Rizvi ................... | C10M 135/10 508/390 |
| 9,688,881 B1 | 6/2017 | Jolley | |
| 2009/0029888 A1 | 1/2009 | Ravichandran et al. | |
| 2015/0057199 A1 | 2/2015 | Yamasaki et al. | |

FOREIGN PATENT DOCUMENTS

| | | |
|---|---|---|
| CN | 102108513 A | 6/2011 |
| CN | 108779557 A | 11/2018 |
| DE | 102019206559 A | 11/2020 |
| DE | 102019210520 A1 | 1/2021 |
| FR | 2930947 A1 | 11/2009 |

* cited by examiner

Figure 1 shows the temerature and humidity as applied during the six day test method.

PRESERVATIVE COMPOSITION

CROSS-REFERENCE TO RELATED APPLICATIONS

This application is the U.S. National Stage of International Application No. PCT/EP2020/062740, filed on May 7, 2020, which claims priority to German patent application no. 102019206560.0 filed on May 7, 2019; each of the above identified applications is hereby incorporated herein by reference as if fully set forth in its entirety.

FIELD OF THE INVENTION

The present invention relates to a preservative composition comprising an anhydride amide and a base oil; the preservative composition comprising in addition a sulfonate composition; a metal article having a coating thereon which coating comprises the preservative composition; and the use of the preservative composition to prevent and/or reduce corrosion in a roll bearing system.

BACKGROUND OF THE INVENTION

Preservative compositions are widely used to protect bearings and other structural components against damages which are the result of for instance corrosion, wear and surface cracking initiation. Damages to bearings and roll bearing systems will affect their performance and functioning during life time at the operating conditions and affects the bearing life.

A common type of bearing damage is fretting. Fretting refers to any situation in which the mating surfaces are subjected to small amplitude reciprocating sliding or rolling motions. Fretting can occur between mating surfaces which are intended to be fixed but are subjected to small oscillating motions to due vibration. In various applications, bearings in housings or bearing on shafts, can be subjected to dynamic loads or bending moments introducing small amplitudes of small amplitudes of relative motion. Fretting can cause seizure, can amplify vibrations, cause wear and fatigue of the components and might eventually lead to failure of the system. Fretting is characterised by the fact that the wear debris stays entrapped in the contact due to the small vibration amplitudes of fretting. In conventional atmospheres, oxidation of the debris is involved and the terms fretting corrosion and fretting wear are often applied. The term false brinelling is specifically used for fretting of point contacts in ball bearings. Bearings of passenger cars can be subjected to small oscillating motions and as a result could reveal false brinelling after car transportation. The appearance of fretting in a ball-on-ring contact resembles a Brinell indentation used in hardness measurements of bulk materials, hence false brinelling. System vibrations and/or cyclic loading, can both result in relative sliding of the mating surfaces over each other and within these aspects two different terminologies are being used. Often a distinction is made between fretting wear and fretting fatigue. Fretting fatigue generally refers to dynamic bulk stresses including tensile stressing of the component. Fretting conditions induce crack initiation and propagation at stresses below the fatigue limit of the component. Fretting wear and fatigue can both involve dynamic loads. Fretting wear is an adhesive wear mechanism. The difference between fretting wear and fatigue is the dominance in which the dynamic bulk stresses (those resulting in tensile stresses) are participating in the failure mode relatively to (dynamic) shear stresses. Such tensile stress can be responsible for through cracking of the component. The shear stresses decrease rather rapidly with the distance beneath the surface and in the absence of tensile bulk stresses, cracking is restricted to shallow surface regions. Under these conditions, fretting wear overshadows fretting fatigue and cracking becomes limited to shallow depths.

Another common type of bearing damage is frictional corrosion which occurs in the form of a chemical reaction which is activated by relative micro movements between contacting surfaces under certain conditions inside a bearing. The frictional corrosion takes place in the form of fretting corrosion or vibration corrosion.

Fretting corrosion occurs when there is a relative movement between a bearing ring and shaft or housing, because e.g. the fit is too loose or too tight. Due to relative movement between the mating surfaces small particles of material may become detached from the surface, and these particles may oxidize quickly when exposed to the oxygen in the atmosphere.

Vibration corrosion, also called false brinelling, occurs in in rolling element-raceway contact areas due to micromovements and/or resilience of the elastic contact under cyclic vibrations. Depending on the intensity of the vibrations, the lubricating condition and load, a combination of corrosion and wear occurs, forming shallow depressions in the raceway. In the case of a stationary bearing, e.g. bearings during transportation of passenger cars, the depressions appear at rolling element pitch and can often be discolored or shiny. Bearing and other metal components are subjected to machining processes, cleaning, heating and other chemical treatments and can face during its production processes various chemical and corrosion aggressive compounds from which the metal surfaces need to be protected.

Another type of corrosion which occurs when bearing rollers face stationary periods such as during transportation or when being installed in the apparatus in which they are to be used. During such periods the bearing rollers do not face micro-movements or oscillating vibration, but nonetheless the bearing rollers may corrode, so-called standstill corrosion.

Rust preventives and corrosion inhibitors are providing limited resistance to these corrosion promoting fluids and environments. After manufacturing the bearing surface can be dipped or sprayed with a preservative fluid. A temporary protecting film can protect the metal and bearing surface against corrosion during transportation and storage of the metal component. A corrosion inhibitor can be applied as an additive in a lubrication oil or grease or even as part of a processing fluid. As long as the carrying fluid or grease is able to make a film over the metal surface than the corrosion inhibitor task is to prevent the surface from corrosion. Rust preventives are usually composed from additives dissolved in a medium. The medium can be as much as 80 wt. % or even higher present in the preservative composition. Popular media are solvents, naphthenic or paraffinic oils. Solvents can have the capacity to completely evaporate while oils usually do not fully evaporate after application and oily films remain on the surface. Water can partially or fully evaporate and as a result could still be part of the final film even after application or drying. Examples of additives used in preservatives are metal salts, waxes, oils, petroleum based products, mineral spirits or other types of additives. Waxes and metal salts are commonly applied as ingredients in the preservatives. Typical examples of metal salts are calcium, barium, sodium sulfonate salts. The use of these typical metal salts do not have fully satisfying corrosion protection and require the need of waxes. Some of these metals salts have their limitation either in use due to their stringent safety and environmental legislations or simply due to their poor corrosion resistance. Waxes are prone to quality inconsistency, unstable crystallinity and can show issues with sprayability.

Conventional preservative compositions are usually composed of metal-containing compounds and waxes. Typical metal-containing compounds used for this purpose are calcium sulfonate salts that are incorporated in the solvent or oil. Another drawback of conventional preservative compositions is the fact that their effectiveness leaves considerable room for improvement.

Object of the present invention is to provide new approach to attractively prevent and/or reduce corrosion in which no use is made of metal salts and waxes. This new approach is based on the preparation of a new chemical composition which displays excellent and resistance to corrosion, in particular moisture corrosion, standstill corrosion and stress corrosion cracking.

Another object of the present invention is to provide a preservative composition which comprises the new chemical composition.

SUMMARY OF THE INVENTION

Surprisingly, it has now found that the use of an anhydride amide in a preservative composition prevents and/or reduces moisture corrosion in an excellent manner.

Accordingly, the present invention provides a preservative composition to prevent and/or reduce corrosion on a metal surface comprising an anhydride-derived amide and an oil and/or a solvent, wherein the anhydride-derived amide is present in an amount in the range of from 0.01.-50 wt %, based on the total weight of the preservative composition.

The preservative composition in accordance with the present invention displays unique properties in terms of moisture corrosion prevention and/or reduction. The present preservative composition prevents and/or reduces moisture corrosion, in particular standstill corrosion in an improved way when compared to conventional preservative compositions that contain calcium sulfonate salts.

BRIEF DESCRIPTION OF THE DRAWINGS

A brief description of the drawings is as follows.

DETAILED DESCRIPTION OF THE INVENTION

Figure 1:
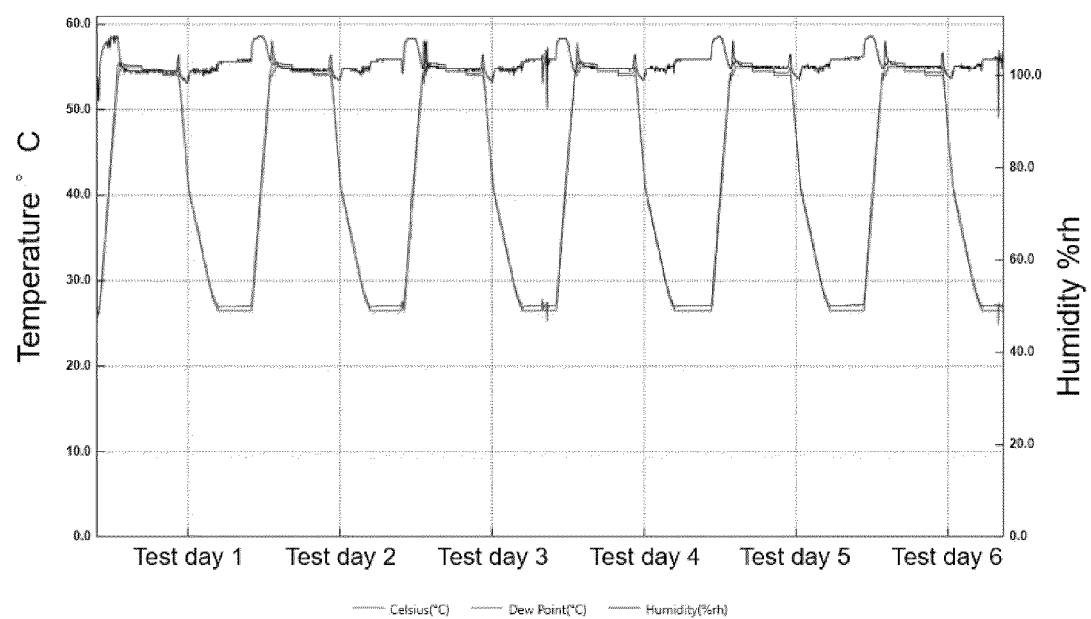
FIG. 1 shows the temperature and humidity as applied during a six day period.

The preservative composition according to the present invention contains an anhydride-derived amide and an oil and/or a solvent, wherein the anhydride-derived amide is present in an amount in the range of 0.01-50 wt. %.

In the context of the present invention an anhydride-derived amide is an amide which is derived from an anhydride by reaction an anhydride with an amine.

Suitable anhydride-derived amides include anhydrides, dianhydrides and trianhydrides, preferably pyromellitic dianhydride amide, succinic acid anhydride amide and maleic acid anhydride amide. Mono-, di-, tri-anhydrides comprise preferably saturated or unsaturated—monounsaturated hydrocarbons or multiple unsaturated hydrocarbons—without or with one or more hydroxyl groups, aliphatic, alicyclic or aromatic hydrocarbons, branched and unbranched hydrocarbons, without or with one or more amine groups, without or with one or more amide groups, amines or amides, and with or without one or more ester groups. Preferred anhydride-derived amides include succinic anhydride-derived amide and maleic anhydride-derived amide.

The anhydride-derived amide to be used in accordance with the present invention suitably has the following general formula (I):

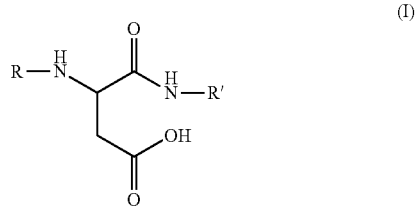

(I)

wherein R and R' each independently represents a hydrocarbon group containing up to 28 carbon atoms. R and R' may be a saturated, unsaturated, aliphatic, alicyclic, aromatic, branched or unbranched hydrocarbon group. The hydrocarbon group may contain one or more hydroxyl groups, one or more amine groups, one or more amide groups and/or one or more ester groups. Preferably, in general formula (I) R and R' each independently represent a saturated unbranched alkyl group containing 2-28 carbon atoms, more preferably it represents a saturated unbranched alkyl group containing 8-18 carbon atoms. Anhydride-derived amide of the general formula (I) can suitably be formed by reacting maleic anhydride in an oil and/or a solvent with an amine or a mixture of amines (R—$NH_2$ and R'—$NH_2$) in a molar ratio 1:2 (maleic anhydride:amine), as shown in the following reaction scheme:

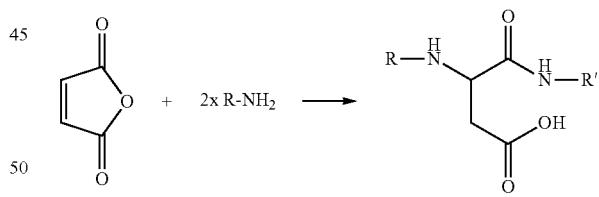

The anhydride-derived amide to be used in accordance with the present invention can also suitably have the following general formula (II):

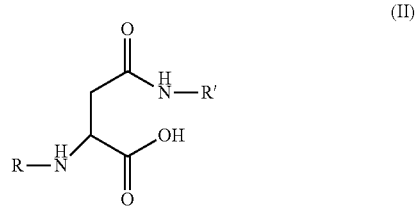

(II)

wherein R and R' each independently represents a hydrocarbon group containing up to 28 carbon atoms. R and R' may be a saturated, unsaturated, aliphatic, alicyclic, aromatic, branched or unbranched hydrocarbon group. The hydrocarbon group may contain one or more hydroxyl groups, one or more amine groups, one or more amide groups and/or one or more ester groups. Preferably, in general formula (II) R and R' each independently represent a saturated unbranched alkyl group containing 2-28 carbon atoms, more preferably it represents a saturated unbranched alkyl group containing 8-18 carbon atoms. Anhydride-derived amide of general formula (II) can suitably be formed by reacting maleic anhydride in an oil and/or a solvent with an amine or mixture of amines (R—NH$_2$ and R'—NH$_2$) in a two steps process with two different amines, two different mechanical and thermal treatments, as shown in the following reaction scheme:

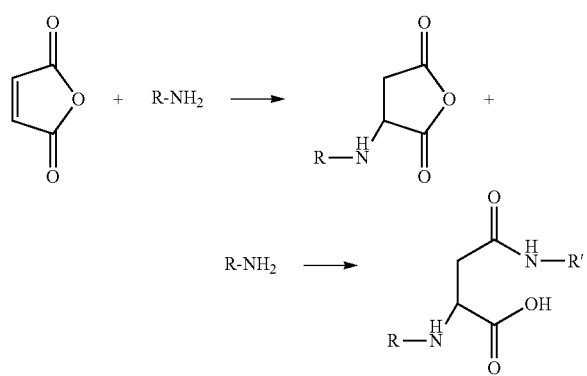

The anhydride-derived amide to be used in accordance with the present invention may also have the following general formula (III):

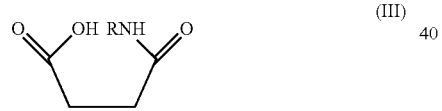

(III)

wherein R represents a hydrocarbon group containing up to 28 carbon atoms. R may be a saturated, unsaturated, aliphatic, alicyclic, aromatic, branched or unbranched hydrocarbon group. The hydrocarbon group may contain one or more hydroxyl groups, one or more amine groups, one or more amide groups and/or one or more ester groups. Preferably, R represents a saturated or unsaturated alkyl group containing 2-28 carbon atoms. More preferably, in general formula (III) R represents a saturated unbranched alkyl group containing 2-28 carbon atoms, even more preferably it represents a saturated unbranched alkyl group containing 8-18 carbon atoms. The anhydride-derived amide of general formula (III) can be prepared by reacting succinic anhydride with an amine in an oil and/or a solvent in a molar ratio of 1 to 1 for amine over anhydride, as shown in the following reaction scheme:

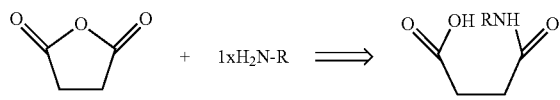

Maleic anhydride can also be reacted with an amine in a molar ratio of 1:3 (anhydride:amine) in an oil and/or a solvent to form an maleic anhydride-derived ammonium salt having the general formulas (IV) and (V), wherein each R, R' and R" each independently represents hydrocarbons up to 28 carbon atoms. The hydrocarbon groups may be saturated, unsaturated, aliphatic, alicyclic, aromatic, branched or unbranched hydrocarbon groups. The hydrocarbon group may contain one or more one hydroxyl groups, one or more amine groups, one or more amide groups and/or one or more ester groups. Preferably, in general formula (IV) R, R' and R" each independently represents a saturated unbranched alkyl group containing 2-28 carbon atoms, more preferably it represents a saturated unbranched alkyl group containing 8-18 carbon atoms. The maleic anhydride-derived ammonium salt of general formulas (IV) can be prepared in accordance with the following reaction scheme, wherein the amine used can be a mixture of R—NH$_2$, R—NH$_2$ and R"—NH$_2$:

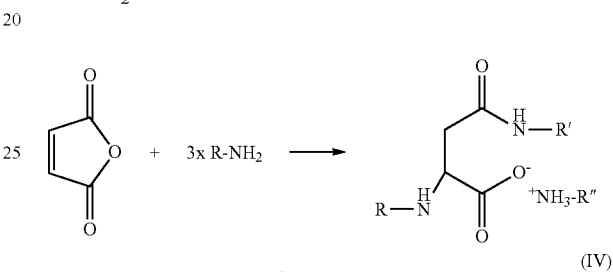

(IV)

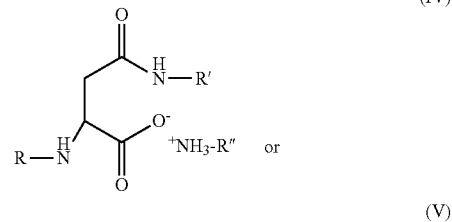

or (V)

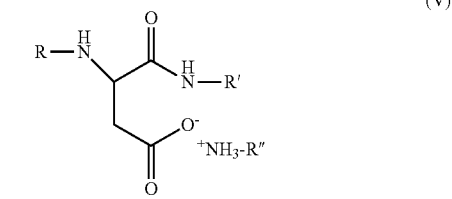

A succinic anhydride-derived ammonium salt of general formula (VI) can also be formed when succinic anhydride is reacted with an amine in an oil and/or a solvent in a molar ratio of 1:2 (anhydride:amine), as shown in the following reaction scheme:

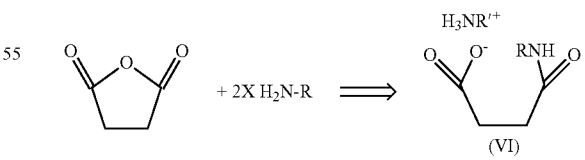

(VI)

In general formula (VI) of the succinic anhydride-derived ammonium salt, R and R' have the same meaning as defined in respect of the maleic anhydride-derived ammonium salts as shown in general formulae (IV) and (V).

At higher temperatures, i.e. at least 120° C., imides can be formed from anhydride-derived ammonium salts as shown in general formulas (IV), (V) and (VI). The imide can have hydrocarbon groups containing up to 28 carbon atoms. The hydrocarbon groups may be saturated, unsaturated, aliphatic, alicyclic, aromatic, branched, unbranched hydrocarbon groups. The hydrocarbon groups may contain one or more hydroxyl groups, one or more amine groups, one or more amide groups and/or one or more ester groups. Preferably, the hydrocarbons in the imide represent a saturated unbranched alkyl group containing 2-28 carbon atoms, more preferably it represents a saturated unbranched alkyl group containing 8-18 carbon atoms. The listed embodiments or any of the preservative compositions according to the present invention comprise any of the here above described components. The imide can have different type of hydrocarbon groups with different functional groups. The ammonium salt can act as a lubricating grease.

The above-mentioned anhydride-derived ammonium salts can also act as a lubricating grease.

When reacting maleic anhydride with an amine in addition to an anhydride-derived amide also an anhydride-derived amine can be formed if the molar ratio is less than 1:2 (maleic acid anhydride:amine). The anhydride-derived amine will have the following general formula (VII) wherein R represents a hydrocarbon group containing up to 28 carbon atoms. R may be a saturated, unsaturated, aliphatic, alicyclic, aromatic, branched or unbranched hydrocarbon group. The hydrocarbon group may contain one or more hydroxyl groups, one or more amine groups, one or more amide groups and/or one or more ester groups.

Preferably, R represents a saturated or unsaturated alkyl group containing 2-28 carbon atoms. Preferably, in general formula (VII) R represents a saturated unbranched alkyl group containing 2-28 carbon atoms, more preferably it represents a saturated unbranched alkyl group containing 8-18 carbon atoms.

The maleic anhydride reaction with the amine may result even at a targeted molar ratio of 1 to 2 (anhydride to amine) in a mixture in which any of the following compounds can be present: anhydride, amine, anhydride-derived amine, anhydride-derived amide and/or an anhydride-derived ammonium salt. Such a mixture is due to improper execution of this reaction or favourable conditions for the formation of any of these ingredients. In bearing operation or other type of rotary equipment operation, friction can also form any of these products. For example, the anhydride-derived amide formed at a molar ratio of 1 to 1 between the succinic anhydride and the amine can lead due to friction or bearing operation to forming any of the additional products. The maleic anhydride reaction with the amine can take place at a molar ratio of preferably 1 to 2 to form the anhydride-derived amide. At a higher molar ratio in addition to the anhydride-derived amide also the anhydride-derived ammonium salt can be formed. At a molar ratio below 2, amines and anhydride can remain in the reaction mixture addition to the amide. Friction can directly change the anhydride-derived amide end product into mixtures of an anhydride-derived ammonium salt and anhydride-derived amides.

The succinic anhydride reaction with the amine may result even at a targeted molar ratio of 1 to 1 in a mixture which may contain any of the following compounds: succinic anhydride, amine, anhydride-derived amide and/or an anhydride-derived ammonium salt. Such a mixture is due to improper execution of this reaction or favourable conditions for the formation of any of these ingredients. In bearing operation or other type of rotary equipment operation, friction can also form any of the products. For example, the amide formed at a molar ratio of 1 to 1 between the succinic anhydride and the amine can lead due to friction or bearing operation to forming any of the additional products. The succinic anhydride reaction with the amine can take place at a molar ratio of preferably 1 to 1 to form the anhydride-derived amide. At a higher molar ratio in addition to the anhydride-derived amide also the anhydride-derived ammonium salt can be formed. At a molar ratio below 1 (amine/anhydride), amines and anhydride can remain in addition to the anhydride-derived amide. Friction can directly change the anhydride-derived amide end product into mixtures of an anhydride-derived ammonium salt and anhydride-derived amides.

The anhydride-derived amide to be used in accordance with the present invention can be prepared by reacting an anhydride with an amine in the presence of an oil and/or a solvent at a temperature in the range of from 20° C.-120° C., preferably, 20-80° C., and wherein the molar ratio of the amine (A1) and the anhydride (A2) is in the range of from 0.2-5 (A1/A2), In bearing operation and operation of other rotary equipment like gears and couplings additional compounds can be formed and/or in dependence of the molar ratio. Anhydride-derived ammonium salt can be formed from at a molar ratio larger than 1 (amine/anhydride).

In case the anhydride is succinic anhydride, the anhydride-derived amide can suitably be prepared by reacting the succinic anhydride with an amine in the presence of an oil and/or a solvent and at a temperature in the range of from 20-120° C., preferably in the range of 20° C.-120° C., preferably 20-80° C., whereby the molar ratio of the amine (A) and the succinic acid anhydride (SAA) is in the range of from 0.2-3 (A/SAA), preferably in the range of 0.5-2.5 (A/SAA), more preferably in the range 0.75-1.25 (A/SAA), and most preferably in the range of from 0.95-1.05, preferably 1 (A/SAA). In bearing operation and operation of other rotary equipment like gears and couplings additional compounds can be formed and/or in dependence of the molar ratio. An anhydride-derived ammonium salt can be formed from at a molar ratio larger than 1 (A/SAA).

In case the anhydride is maleic anhydride, the anhydride-derived amide can suitably be prepared by reacting the maleic anhydride with an amine in the presence of an oil and/or a solvent and at a temperature in the range of from 20° C.-120° C., preferably 20-80° C., whereby the molar ratio of the amide (A) to maleic acid anhydride (MAA) is in the range of from 0.5-5 (A/MAA), preferably in the range of from 1-2.5 (A/MAA), more preferably in the range of from 1-2.25 (A/MAA), and most preferably in the range of from 1.95-2.05, preferably 2 (A/MAA). In bearing operation and operation of other rotary equipment like gears and couplings additional compounds can be formed and/or in dependence of the molar ratio. An anhydride-derived ammonium salt can be formed from at a molar ratio larger than 2 (A/MAA).

The maleic anhydride-derived amide or succinic anhydride-derived amide is prepared by reacting the maleic anhydride and/or the succinic anhydride with the amine in the presence of an oil and/or a solvent at a temperature in the range of from 20-120° C., preferably in the range of from 20-80° C., preferably in the range of from 30-80° C., more preferably in the range of from 40-80° C., and most preferably in the range of from 50-70° C.

Preferably, the amine to be used in accordance with the present invention is a fatty acid amine. In the context of the present application fatty acid amines are defined as amines derived from fatty acids wherein the fatty acid represents hydrocarbon fatty acids that contain up to 28 carbon atoms. The fatty acids may be saturated, unsaturated, aliphatic, alicyclic, aromatic, branched, unbranched fatty acids. The fatty acids may contain one or more hydroxyl groups, one or more amine groups, one or more amide groups and/or one or more ester groups. Preferably, the fatty acid is a saturated unbranched fatty acid containing 2-28 carbon atoms, more preferably it is saturated unbranched fatty acid containing 8-18 carbon atoms. It will be understood that fatty acids are aliphatic monocarboxylic acids derived from, or contained in esterified form in an animal or vegetable fat, oil or wax. In accordance with the present invention use can be made of natural and synthetic fatty acids. Suitably, the amine to be used in accordance with the present invention is a saturated fatty acid amine or it contains one or more unsaturated C—C bonds in which a $NH_2$ group is introduced somewhere in the unsaturated fatty acid chain. The fatty acid amines may be saturated, unsaturated, aliphatic, alicyclic, branched and/or unbranched. Preferably, the fatty acid amine is unbranched and contains 2-28 carbon atoms, more preferably 8-18 carbon atoms. Preferably, the fatty acid amine is unbranched and saturated and contains 2-28 carbon atoms, more preferably 8-18 carbon atoms.

Primary, secondary, tertiary and cyclic amines exist. Organic amines include amino acids, trimethylamine, aniline and biogenic amines. Fatty amines has an amine attached to a hydrocarbon chain and the fatty amines is part of the oleochemical functional groups being derived from plant and animal fats.

The amines to be used in accordance with the present invention can for instance be formed from ammonia in an alkylation reaction with alcohol in the presence of ammonia and in the presence of catalysts. Hydrogenation reduces nitriles to amines in the presence of a catalyst. Reaction of haloalkanes with ammonia and amines forms different type of amines. Lithiumaluminiumhydride reduces amides to amines. Many amines are produced from aldehydes and ketones via reductive amination, which can either proceed catalytically or stoichiometrically. Ammonium salts which can provides beneficial effects to the grease composition of the present invention can be formed from amines and halocarbons.

The amines may also be formed by the hydrolysis of alkyl isocyanate, or by degradation of the acid amide with aid of hypochlorite, hypobromite, halogen, or in combination with a base, the conversion of the corresponding acid azide with aid of an acid chloride with sodium azide resulting in amine hydrochloride, or reduction of a cyanide or of acid amide.

Commonly applied amines can originate from aliphatic, alicyclic and aromatic, saturated and unsaturated, branched and unbranched amines.

The preferred embodiments of the present invention have a $NH_2$ at the end of the hydrocarbon chain. Aliphatic, aromatic, saturated, unsaturated, branched or unbranched or other type of amines are part of the present invention as long as one end of the hydrocarbon chain has a $NH_2$ configuration.

An aliphatic unsaturated fatty amine comprises preferably 2-28 carbon atoms.

Commonly applied amines can originate from saturated and unsaturated fatty acids like lauric acid, myristic acid, palmitic acid, stearic acid, arachidic acid, behenic acid, lignoceric acid, lauroleic acid, myristoleic acid, palmitoleic acid, gadoleic acid, erucic acid, ricinoleic acid, linoleic acid, linolenic acid, eleostearic acid, arachidonic acid, phenylstearylamine and clupadonic acid. The amines of the foregoing acids may be obtained by transformation to the acid amide followed by reduction with sodium in absolute alcohol. Other sources of mixed amines are known to the art.

The unsaturated fatty amines as part of the here presented invention are prepared and formed from ammonia of which one or two hydrogens are substituted by hydrocarbon chain of a length from 18 C-atom or more and having 1 to 3 unsaturated carbon bonds. Commercial unsaturated fatty amines are blends of fatty amine of various hydrocarbon chain length and comprising of 1 to 3 unsaturated carbon bonds. These blended compositions can have various wt. % of unsaturated fatty amines. These mixed fatty amines can be further processed to obtain the desired quantity of unsaturated amines and to control these amounts by applied processing techniques of decanting, steam distillation or other processing techniques. Examples of unsaturated fatty amines are oleylamine, linoleylamine, linolenylamine, arachidylamine, eleostearylamine, erucylamine, petroselenylamine, and palmitoleylamine. The amine to be used can be saturated or unsaturated, branched or unbranched C2-C28 amines. Preferably, the C2-C28 amines are saturated amines.

Suitably, the amines to be used in accordance with the present invention contain amines up to 28 carbon atoms. Suitably, the are saturated, unsaturated, aliphatic, alicyclic, aromatic, branched or unbranched amines. The amines may contain one or more hydroxyl groups, one or more amine groups, one or more amide groups and/or one or more ester groups.

Suitably, the saturated fatty acid amines from which the preservatives in accordance with the present invention can be made contain at least one OH group.

Suitable examples of such amines are ethyl hydroxy stearamine and bishydroxyethyl oleylamine, and diamines such as bishydroxyethyl oleylamine.

Suitably, the amines contain two or more unsaturated C—C bonds.

Suitably, the amines contain two or more unsaturated C—C bonds and at least one OH group, preferably at least two OH groups. Suitably, the unsaturated amines further include at least one OH-group. Suitable examples of such amines are ethyl hydroxy stearamine and bishydroxyethyl oleylamine, and diamines such as bishydroxyethyl oleylamine. Diamines affects the molar ratio, but a person expert in the here presented field of expertise will understand that the molar ratio is affected. This variable is part of the invention although not further explained.

The amines may contain an ester group.

The amine to be used is suitably selected from the group consisting of stearylamine, butylamine, pentylamine, hexylamine, heptylamine, amine and octylamine.

The present preservative composition comprises an oil and/or a solvent, and the anhydride-derived amide is made by reacting an anhydride with an amine in the presence of an oil and/or a solvent. Suitably, the oil is a base oil. Preferably, the preservative composition comprises an anhydride-derived amide and a base oil, wherein the anhydride-derived amide is present in an amount in the range of from 0.01-50 wt. %, based on the total weight of the preservative composition. In the preservative composition, the oil and/or solvent is suitably present in an amount in the range of 70-99 wt. %, preferably in the range of from 85-99 wt. %, and more preferably in the range of from 93-98 wt. %, based on the total weight of the preservative composition. A variety of base oils can be used, provided that they provide a good solubility. Suitable examples of base oils include Group I, II, III, IV and V oils, and polyalfaolefins. Preferably, the base oil comprises polyalfaolefins or alkylated naphthalene.

In accordance with the present invention also use can be made of one or more solvents. Preferably, the one or more solvents are selected from the group consisting of polar solvents, non-polar solvents and aprotic polar solvents. Suitable examples of polar solvents include formic acid, n-butanol, isopropanol, nitromethane, ethanol, methanol, acetic acid and water. Suitable examples of non-polar solvents include hexane, benzene, toluene, 1,4-dioxane, chloroform and diethyl ether. Suitable solvents of aprotic solvents include dichloromethane, N-methylpyrrolidone, tetrahydrofuran, ethyl acetate, acetone, dimethylformamide, acetonitrile, dimethyl sulfoxide and propylene carbonate. Preferred solvents to be used in accordance with the present invention include dimethyl sulfoxide, acetone, chloroform, ethyl ether, n-hexane, benzene, N-methyl-2-pyrrolidone, dimethylformamide, dimethylacetamide, N-methyl-2-pyrolidone and water.

In accordance with the present invention the preservative composition may also include an emulsifier. The emulsifier is suitably present in an amount in the range of from 0.01-30 wt. %, preferably in the range of from 2-20 wt. %, and more preferably in the range of from 5-15 wt. %, based on the total weight of the preservative composition.

The emulsifier can be anionic; it may be a sulfate, sulfonate, or phosphate ester; it may contain cationic head groups; it may include zwitterionic surfactants; it may be nonionic. Suitable examples include ethoxylates such as fatty alcohol ethoxylates; special ethoxylated fatty esters and oils; ethoxylated amines and/or fatty acid amides; and terminal blocked ethoxylates. Other suitable examples of emulsifiers include fatty acid esters of polyhydroxy compounds such as fatty acid esters of polyhydroxy compounds; fatty acid esters of glycerol; fatty acid esters of sorbitol; fatty acid esters of sucrose; and alkyl polyglucosides. Other suitable emulsifiers include amine oxided, sulfoxides, and phosphide oxides such as sodium phosphates; mono- and diglycerides; sodium stearoyl lactylate; esters of monoglyceride; and simple cellulose.

The present invention can comprise mixture of above listed type of emulsifiers or can contain waxes such as for instance polyethylene or oxidised polyethylene.

In a particularly attractive embodiment of the present invention the preservative composition comprises in addition a sulfonate composition.

Hence, the present invention also relates to a preservative composition comprising an anhydride-derived amide, a sulfonate composition and an oil and/or a solvent, wherein the sum of the amounts of the anhydride-derived amide and the sulfonate composition is in the range of from 0.01-50 wt. %, preferably in the range of from 1-30 wt. %, and more preferably in the range of from 1-10 wt. %, based on the total weight of the preservative composition.

The sulfonate composition to be used in accordance with the present invention is obtainable by a process in which an aromatic ring-containing sulfonic acid is reacted with an amine in the presence of an oil and/or a solvent at a temperature in the range of from 20-120° C., preferably 20-80° C., and wherein the molar ratio of the sulfonic acid (S) to the amide (A) is in the range of from 0.2-3 (S/A).

Suitably, the sulfonate composition is present in an amount in the range of from 0.01-50 wt. %, preferably in the range of from 0.01-20 wt. %, and more preferably in the range of from 0.01-10 wt. %, based on the total weight of the preservative composition.

If the preservative composition comprises the anhydride-derived amide, the sulfonate composition and an oil and/or a solvent, the oil and/or solvent is (are) suitably present in an amount in the range of 50-99.99 wt. %, preferably in the range of from 70-99 wt. %, and more preferably in the range of from 90-99 wt. %, based on the total weight of the preservative composition.

Preferably, the sulfonate composition is a naphthalene ring-containing sulfonate composition comprising up to 30 carbon atoms, preferably up to 16 carbon atoms or preferably up to 10 carbon atoms. Suitable examples include napthalene-1-sulfonic acid and naphthalene-2-sulfonic acid.

The sulfonate composition—sulfonic acid-derived amide—to be used in accordance with the present invention has suitably the following general formula (VIII)

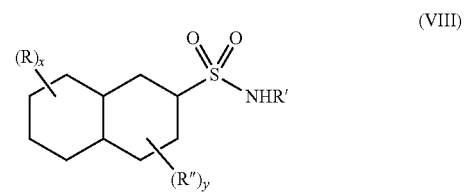

wherein R' represents hydrocarbon group which contains up to 30 carbon atoms, preferably up to 16 carbon atoms, more preferably up to 10 carbon atoms and R and R" each independently represents a hydrocarbon group containing up to 28 carbon atoms or a hydroxyl group, and wherein x is in the range of from 0-4 and y is in the range of from 0-3. R and R" may be at one or more positions in the respective rings. R', R" and R may independently be a saturated, unsaturated, aliphatic, alicyclic, aromatic, branched or unbranched hydrocarbon group. R', R" and R may each independently contain one or more hydroxyl groups, one or more amine groups, one or more amide groups and/or one or more ester groups. R', R" and R each independently represents preferably a saturated or unsaturated hydrocarbon group containing 2-28 carbon atoms. Preferably, R', R" and R each independently represents a saturated unbranched hydrocarbon group containing 2-28 carbon atoms, more preferably it represents a saturated unbranched alkyl group containing 8-22 carbon atoms. R, R" and R' may be different. R and R" may be absent in general formula VIII. The sulfonate composition of general formula (VIII) can be prepared by reacting sulfonic acid with an amine in a molar ratio of 1:1.

The sulfonate composition to be used in accordance with the present invention can be obtained by reacting a sulfonic acid with an amine in the presence of an oil and/or a solvent and at a temperature of 20-120° C., preferably 20-80° C., and wherein the molar ratio of the sulfonic acid (S) to the amine (A) is in the range of from 0.2-3 (S/A).

The preferred sulfonate composition is a sulfonate ammonium salt having the following general formula (IX):

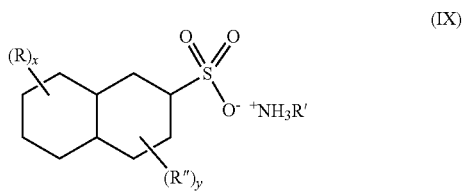

wherein R' represents a hydrocarbon group which contains up to 30 carbon atoms, preferably up to 16 carbon atoms, more preferably up to 10 carbon atoms and R and R" each independently represents a hydrocarbon group containing up to 28 carbon atoms or a hydroxyl group, wherein x is in the range of from 0-4 and y is in the range of 0-3. R and R" may be at one or more positions in the respective rings. R' and R" may each independently be a saturated, unsaturated, aliphatic, alicyclic, aromatic, branched or unbranched hydrocarbon group. R', R and R may each independently contain one or more hydroxyl groups, one or more amine groups, one or more amide groups and/or one or more ester groups. R', R" and R each independently represents preferably a saturated or unsaturated hydrocarbon group containing 2-28 carbon atoms. Preferably, R', R" and R each independently represents a saturated unbranched hydrocarbon group containing 2-28 carbon atoms, more preferably it represents a saturated unbranched hydrocarbon group containing 8-22 carbon atoms. R and R' may be different. R and R" may be absent in general formula IX. The sulfonate salt composition of general formula (IX) can be prepared by reacting sulfonic acid in the presence of an oil and/or a solvent with an amine in a molar ration of 1:1.

This sulfonate ammonium salt can act as a lubricating grease and can be present in the composition of the present invention.

The sulfonate composition to be used in accordance with the present invention can be obtained by reacting a sulfonic acid with an amine in the presence of an oil and/or a solvent and at a temperature of 20-120° C., preferably 20-80° C., and wherein the molar ratio of the sulfonic acid (S) to the amine (A) is in the range of from 0.2-3 (S/A). Mixtures of one or more oils and/or one or more solvents can be used in accordance with the invention.

Suitably, the oil is a base oil. Preferably, the preservative composition comprises an anhydride-derived amide and a base oil, wherein the anhydride-derived amide is present in an amount in the range of from 0.01-50 wt. %, based on the total weight of the preservative composition. In the preservative composition, the oil and/or solvent is suitably present in an amount in the range of 70-99 wt. %, preferably in the range of from 85-99 wt. %, and more preferably in the range of from 93-98 wt. %, based on the total weight of the preservative composition. A variety of base oils can be used, provided that they provide a good solubility. Suitable examples of base oils include Group I, II, III, IV and V oils, and polyalfaolefins. Preferably, the base oil comprises polyalfaolefins or alkylated naphthalene.

In accordance with the present invention also use can be made of one or more solvents. Preferably, the one or more solvents are selected from the group consisting of polar solvents, non-polar solvents and aprotic polar solvents. Suitable examples of polar solvents include formic acid, n-butanol, isopropanol, nitromethane, ethanol, methanol, acetic acid and water. Suitable examples of non-polar solvents include hexane, benzene, toluene, 1,4-dioxane, chloroform and diethyl ether. Suitable solvents of aprotic solvents include dichloromethane, N-methylpyrrolidone, tetrahydrofuran, ethyl acetate, acetone, dimethylformamide, acetonitrile, dimethyl sulfoxide and propylene carbonate. Preferred solvents to be used in accordance with the present invention include dimethyl sulfoxide, acetone, chloroform, ethyl ether, n-hexane, benzene, N-methyl-2-pyrrolidone, dimethylformamide, dimethylacetamide, N-methyl-2-pyrolidone and water.

Preferably, the aromatic ring-containing sulfonic acid is a naphthalene ring-containing sulfonic acid. Good results can also be achieved with linear alkylbenzene sulfonic acid, branched alkylbenzene sulfonic acids or with or without unsaturated bonds in the hydrocarbon chain.

The sulfonate composition to be used in accordance with the present invention can be prepared by reacting an aromatic ring-containing sulfonic acid with an amine. The sulfonic acid can be aliphatic, branched, unbranched, saturated or unsaturated, aromatic as long as the end of the hydrocarbon chain has the sulfonic configuration.

Preferred embodiments of the present invention are naphthalene sulfonic acid, anthracene sulfonic acid, phenanthrene sulfonic acid and benzene sulfonic acids.

The naphthalene ring-containing sulfonic acid is suitably selected from the group consisting of naphthalene sulfonic acid, anthracene sulfonic acid, and phenanthrene sulfonic acid. Preferably, the naphthalene ring-containing sulfonic acid is naphthalene sulfonic acid.

In the process for preparing the sulfonate composition to be used in accordance with the present invention, the temperature is in the range of from 20-120° C., preferably in the range of from 20-80° C., more preferably in the range of from 30-80° C., more preferably in the range of from 40-80° C., and most preferably in the range of from 50-70° C.

In the process for preparing the sulfonate composition, the molar ratio of the amine (A) to the sulfonic acid (S) is in the range of from 0.2-3 (A/S), preferably in the range of from 0.6-1 (A/S), more preferably in the range of from 0.6-1 (A/S), and most preferably 0.9-1.1 (A/SA).

Preferably, the sulfonate composition is prepared by reacting naphthalene sulfonic acid with aliphatic amine in the presence of a base oil.

In a preferred embodiment of the present invention the preservative composition comprises a succinic anhydride-derived amide and/or maleic anhydride-derivable amide, a sulfonate ammonium salt and an oil and/or a solvent, wherein the maleic anhydride-derived amide and/or succinic anhydride-derived amide is present in an amount of 0.01-30 wt. %, and the sulfonate ammonium salt is present in an amount of 0.01-30 wt. %, both based on the total weight of the preservative composition; and wherein the sulfonate salt has the following general formula (IX):

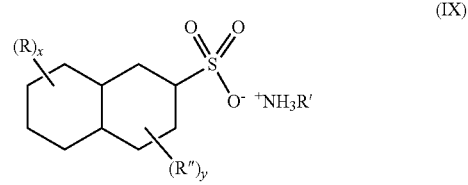

wherein R' represents a hydrocarbon group which contains up to 30 carbon atoms, preferably up to 16 carbon atoms, more preferably up to 10 carbon atoms and R and R" each independently represents a hydrocarbon group containing up to 28 carbon atoms or a hydroxyl group, and wherein x ranges from 0-4 and y ranges from 0-3. R', R and R may each independently be a saturated, unsaturated, aliphatic, alicyclic, aromatic, branched or unbranched hydrocarbon group. R', R and R may each independently contain one or more hydroxyl groups, one or more amine groups, one or more amide groups and/or one or more ester groups. R' and R represents preferably a saturated or unsaturated alkyl group containing 2-28 carbon atoms. More preferably, R' and R represents a saturated unbranched alkyl group containing 2-28 carbon atoms, even more preferably it represents a saturated unbranched alkyl group containing 8-22 carbon atoms. R and R' may be different. R and R" may be absent.

In a preferred embodiment of the present invention the preservative composition comprises maleic anhydride-derived amide, a sulfonate ammonium salt and an oil and/or a solvent, wherein the maleic anhydride-derived amide is present in an amount of 0.01-30 wt. %, and the sulfonate ammonium salt is present in an amount of 0.01-30 wt. %, both based on the total weight of the preservative composition; and wherein the sulfonate ammonium salt has the following general formula (IX):

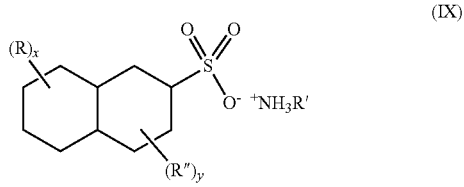

wherein R' represents a hydrocarbon group which includes a naphthalene ring which contains up to 30 carbon atoms, preferably up to 16 carbon atoms, more preferably up to 10 carbon atoms and R and R' each independently represents a hydrocarbon group containing up to 28 carbon atoms or a hydroxyl group, and wherein x is in the range of from 0-4 and y is in the range of from. R, R and R' may each independently be a saturated, unsaturated, aliphatic, alicyclic, aromatic, branched or unbranched hydrocarbon group. R, R" and R' may each independently contain one or more hydroxyl groups, one or more amine groups, one or more amide groups and/or one or more ester groups. R, R" and R' each independently represents preferably a saturated or unsaturated alkyl group containing 2-28 carbon atoms. Preferably, R, R" and R' each independently represents a saturated unbranched alkyl group containing 2-28 carbon atoms, more preferably it represents a saturated unbranched alkyl group containing 8-22 carbon atoms. R, R" and R' may be different. R and R" may be absent.

Depending on the condition in which the reaction takes place, the sulfonate composition of general formulas (VIII) and/or the sulfonate ammonium salt of general formula (IX) is formed.

The sulfonic acid reaction with the amine may result even at a targeted molar ratio of 1 to 1 in a mixture in which any of the following compounds can be present: sulfonic acid, amine, sulfonic acid-derived amide and/or ammonium salt. Such a mixture is due to improper execution of this reaction or favourable conditions for the formation of any of these ingredients. In bearing operation or other type of rotatory equipment operation, friction can also form any of these products. For example, the anhydride-derived amide formed at a molar ratio of 1 to 1 between the succinic anhydride and the amine can lead due to friction or bearing operation to forming any of the additional products. The sulfonic acid reaction with the amine can take place at a molar ratio of preferably 1 to 1 (sulfonic acid to amine) to form the sulfonic acid amide and/or sulfonate ammonium salt. At a higher molar ratio than 1 to 1 in addition the ammonium salt can be formed. At a molar ratio below 1, amines and anhydride can remain in the reaction mixture addition to the amide. Friction can directly change the anhydride-derived amide end product into mixtures of an anhydride-derived ammonium salt and anhydride-derived amides. At any improper execution of the reactions between the sulfonic acid and the amine either at a molar ratio of 1 to 1 (sulfonic acid to amine) or due to friction can lead to a mixture of products: sulfonic acid, amine, sulfonic acid-derived amide and/or ammonium salt.

In addition to the sulfonate composition, the solvents and emulsifiers described above, the preservative composition according to the present invention may contain additives such as corrosion inhibitors and lubricating improvers.

The amine to be used in the preparation of the sulfonate composition to be used in the present invention is preferably a fatty acid amine as defined here before.

The preferred amines have a $NH_2$ at the end of the hydrocarbon chain. Aliphatic, aromatic, saturated, unsaturated, branched or unbranched or other type of amines are part of the present invention as long as one end of the hydrocarbon chain has a $NH_2$ configuration.

An aliphatic unsaturated fatty amine comprises preferably 2-28 carbon atoms.

Commonly applied amines can originate from saturated and unsaturated fatty acids like lauric acid, myristic acid, palmitic acid, stearic acid, arachidic acid, behenic acid, lignoceric acid, lauroleic acid, myristoleic acid, palmitoleic acid, gadoleic acid, erucic acid, ricinoleic acid, linoleic acid, linolenic acid, eleostearic acid, arachidonic acid, phenylstearylamine and clupadonic acid. The amines of the foregoing acids may be obtained by transformation to the acid amide followed by reduction with sodium in absolute alcohol. Other sources of mixed amines are known to the art.

The unsaturated fatty amines as part of the here presented invention are prepared and formed from ammonia of which one or two hydrogens are substituted by hydrocarbon chain of a length from 18 C-atom or more and having 1 to 3 unsaturated carbon bonds. Commercial unsaturated fatty amines are blends of fatty amine of various hydrocarbon chain length and comprising of 1 to 3 unsaturated carbon bonds. These blended compositions can have various wt. % of unsaturated fatty amines. These mixed fatty amines can be further processed to obtain the desired quantity of unsaturated amines and to control these amounts by applied processing techniques of decanting, steam distillation or other processing techniques. Examples of unsaturated fatty amines are oleylamine, linoleylamine, linolenylamine, arachidylamine, eleostearylamine, erucylamine, petroselenylamine, and palmitoleylamine. The amine to be used can be saturated or unsaturated, branched or unbranched C2-C28 amines. Preferably, the C2-C28 amines are saturated amines.

Suitably, the amines to be used in accordance with the present invention contain one or more unsaturated C—C bonds and/or at least one OH group.

Suitably, the amines to be used in accordance with the present invention contain one or more unsaturated C—C bonds and at least one OH group.

Suitably, the amines contain two or more unsaturated C—C bonds.

Suitably, the amines contain two or more unsaturated C—C bonds and at least one OH group, preferably at least two OH groups. Suitably, the unsaturated amines further include at least one OH-group. Suitable examples of such amines are ethyl hydroxy stearamine and bishydroxyethyl oleylamine, and diamines such as bishydroxyethyl oleylamine. Diamines affects the molar ratio, but a person expert in the here presented field of expertise will understand that the molar ratio is affected. This variable is part of the invention although not further explained.

The one or more unsaturated amines may suitably in addition contain at least one OH group, suitably at least two OH groups. Suitably, the one or more amines contain two or more unsaturated C—C bonds and at least one OH group. Suitably, the one or more amines are metal salts. The amines may contain an ester group.

The amine to be used is suitably selected from the group consisting of stearylamine, butylamine, pentylamine, hexylamine, heptylamine, amine and octylamine.

The present invention also relates to a metal article having a coating thereon which coating comprises the preservative composition according to the present invention. Suitably, the metal article is a rolling element. Preferably, the metal article is a bearing. An advantage of the sulfonate composition according to the present invention is that it has very attractive film forming properties which allows for excellent coatings to be formed on the metal articles.

The preservative composition according to the present invention can be used to prevent and/or reduce corrosion, in particular moisture corrosion, standstill corrosion, stress corrosion cracking or any other form of corrosion on a metal surface. Suitable metal surfaces are surfaces of metal articles like housing bearing seats, shaft bearing seats, spacer surfaces, guidering surfaces, seal surfaces, seal seat surfaces or any other surfaces that are facing oscillating motions and/or vibrations and/or any forms of corrosion. The preservative composition according to the present invention can be used on the surfaces of metal articles but also on non-metal surfaces like plastic material surfaces, glass material surfaces and plastic material surfaces.

In addition, the present invention relates to the use of the present preservative composition for preventing and/or reducing moisture corrosion, stress corrosion cracking, in particular standstill corrosion, in a roll bearing system and its components, coupling system and its components, gear system and its components.

Further, the present invention relates to the use of the preservative composition according to the present invention for preventing and/or reducing moisture corrosion, in particular standstill corrosion, in a roll bearing system.

EXAMPLES

The spherical bearing rollers to be tested in the Examples were first placed in a climate corrosion chamber. The rollers were then cleaned using the cleaning process described here below prior to dipping the rollers into the preservative as described in Examples 1-10, and testing the dipped rollers.

Cleaning Process
1) 3 minutes cold cleaning of the rollers in ultrasonic bath with Petroleum Ether (PE) 80/110 at room temperature.
2) Wipe off liquid with tissue paper from rollers, repeat wiping off till the tissue remains white.
3) Clean the rollers with Iso-Propyl-Alcohol (IPA) with tissue at room temperature.
4) Rinse off the surface of the rollers with IPA.
5) Dry the rollers without rubbing in an oven (60-80° C.) for 30 min.
6) Cool the rollers for at least 30 minutes but no longer than 24 hours in an exsiccator/dehydrator to remove IPA from the surface of the rollers.

The cleaned rollers are than dipped in the respective preservatives as described in Examples 1-10, and kept overnight at room temperature.

The dipped rollers were then tested according to the test method IEC-60068-2-30-TEST-DB-Variante 1.

Example 1

First, maleic anhydride is reacted with an amine.

Octadecylamine (from Alfa Aesar CAS nr 214-30-1) was reacted with maleic anhydride (from Sigma Aldrich CAS nr 108-31-6) in a molar ratio of 2:1 (amine:maleic anhydride). This reaction was carried out in alkylated naphthalene Na-Lube KR 008 oil (from King Industries Inc) for a few minutes. The reaction has been run at a temperature of 70° C.

A second reaction is carried out between naphtalene-2-sulfonic acid and octadecylamine. The naphthalene-2-sulfonic acid with CAS nr 120-18-3 is sourced from Alfa Aesar. The octadecylamine CAS nr 214-30-1 was sourced from Alfa Aesar. The reaction has a molar ratio of naphthalene-2-sulfonic acid to octadecylamine 1:1. The reaction was carried out for a few minutes at a temperature of 70° C. in alkylated naphthalene Na-Lube KR 008 oil (from King Industries Inc).

The first reaction product was then in equal amounts blended with the second reaction product. The final preservative composition consisted of 90.7 wt. % Nalube oil, 5 wt. % maleic anhydride-derived amide and 4.3 wt. % sulfonic acid-derived amide.

Figure 2:
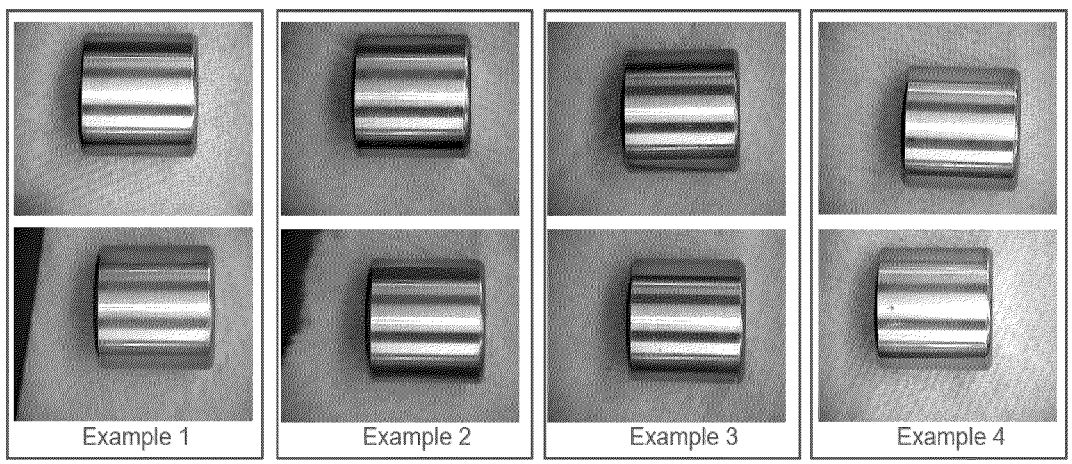
FIG. 2 shows 4 examples of roller pairs.

Five rollers were then dipped into the final preservative. The dipped rollers then tested for 6 days according to the described cleaning method and the climate corrosion method IEC-60068-2-30-TEST-DB-Variante 1. Two rollers out of the five rollers are shown in FIG. 2. The five rollers showed no corrosion while one roller showed a single corrosion spot. Five rollers dipped in Na-Lube KR 008 oil showed all five signs of corrosion.

Figure 5:
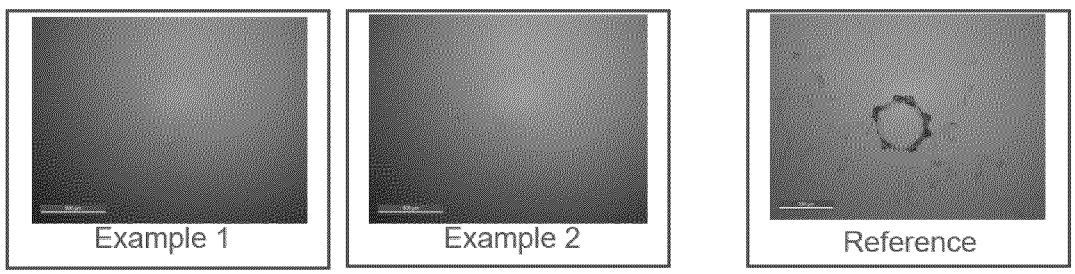
FIG. 5 shows the results of the standstill corrosion test.

One of the five dipped rollers was also subjected to a standstill corrosion test. The standstill corrosion test was performed pressing a bearing ball ½" in diameter against a flat bearing steel plate. This ball-in-contact-with-plate configuration was placed in a corrosive environment at 75° C. for 3 days. The steel plate was visually examined for corrosion marks, corrosion contact circle and corrosion spots. No corrosion spots were observed for this roller after the standstill corrosion test. The result of this test is shown in FIG. 5. The reference sample showed standstill corrosion marks (contact circle) after the test. This reference sample was a lithium thickened grease with a mineral base of oil 120 cSt at 40° C. The reference sample showed a typical standstill corrosion mark (see FIG. 5).

Example 2

First, maleic anhydride is reacted with an amine.

Dodecylamine (from Alfa Aesar CAS nr 124-22-1) reacted with maleic anhydride (from Sigma Aldrich CAS nr 108-31-6) in a molar ratio of 2:1 (amine:maleic anhydride). This reaction was carried out in alkylated naphthalene Na-Lube KR 008 oil (from King Industries Inc) for a few minutes. The reaction has been run at a temperature of 70° C.

A second reaction was then carried out between naphtalene-2-sulfonic acid and octadecylamine. The naphthalene-2-sulfonic acid with CAS nr 120-18-3 is sourced from Alfa Aesar. The octadecylamine CAS nr 214-30-1 was sourced from Alfa Aesar. The reaction has a molar ratio of naphthalene-2-sulfonic acid to octadecylamine 1:1. The reaction was carried out for a few minutes at a temperature of 70° C. in alkylated naphthalene Na-Lube KR 008 oil (from King Industries Inc).

The first reaction product was then blended in equal amounts with the second reaction product, and mixed with extra Nalube oil.

The final preservative composition consisted of 92 wt. % Nalube oil, 4.3 wt. % maleic anhydride-derived amide and 3.7 wt. % sulfonic acid-derived amide.

Five rollers were then dipped into the final preservative. The dipped rollers then tested for 6 days according to the described cleaning method and the climate corrosion method IEC-60068-2-30-TEST-DB-Variante 1. The rollers so obtained are shown in FIG. 2. The five rollers did not show any corrosion. Five rollers dipped in Na-Lube KR 008 oil showed all five signs of corrosion.

One of the five dipped rollers was also subjected to a standstill corrosion test. The standstill corrosion test was performed pressing a bearing ball ½" in diameter against a flat bearing steel plate. This ball-in-contact-with-plate configuration was placed in a corrosive environment at 75° C. for 3 days. The steel plate was visually examined for corrosion marks, corrosion contact circle and corrosion spots. No corrosion spots were observed for this roller after the standstill corrosion test. The result of this test is shown in FIG. 5. The reference sample showed standstill corrosion marks (contact circle) after the test. This reference samples was a lithium thickened grease with a mineral base of oil 120 cSt at 40° C. The reference sample showed a typical standstill corrosion mark (see FIG. 5).

Example 3

First, succinic anhydride was reacted with an amine.

Octadecylamine (from Alfa Aesar CAS nr 214-30-1) reacted with succinic anhydride (from Alfa Aesar CAS nr 108-30-5) in a molar ratio of 1:1.

This reaction was carried out in alkylated naphthalene Na-Lube KR 008 oil (from King Industries Inc) for a few minutes. The reaction was carried out at a temperature of 70° C.

A second reaction was then carried out between naphtalene-2-sulfonic acid and octadecylamine. The naphthalene-2-sulfonic acid with CAS nr 120-18-3 was sourced from Alfa Aesar. The octadecylamine CAS nr 214-30-1 was sourced from Alfa Aesar. The reaction has a molar ratio of naphthalene-2-sulfonic acid to octadecylamine 1:1. The reaction was carried out for a few minutes at a temperature of 70° C. in alkylated naphthalene Na-Lube KR 008 oil (from King Industries Inc).

The first reaction product was then blended in equal amounts blended with the second reaction product, and mixed with extra Nalube oil.

The final preservative composition consisted of 94.4 wt. % Nalube oil, 3.0 wt. % succinic anhydride-derived amide and 2.6 wt. % sulfonic acid-derived amide.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 2. Four rollers showed no corrosion, whilst one roller showed one single corrosion spot. Five rollers dipped in Na-Lube KR 008 oil showed all five signs of corrosion.

Example 4

First, maleic anhydride was reacted with an the amine.

Octadecylamine (from Alfa Aesar CAS nr 214-30-1) was reacted with maleic anhydride (from Sigma Aldrich CAS nr 108-31-6) in a molar ratio of 2:1 (amine:maleic anhydride).

This reaction was carried out in PAO 68 cSt (INEOS) for a few minutes. This PAO is a blend of PAO 46—Durasyn 168—and PAO 400—Durasyn 174—both PAO products were sourced from INEOS. The reaction was carried out at a temperature of 70° C.

A second reaction was then carried out between naphtalene-2-sulfonic acid and octadecylamine. The naphthalene-2-sulfonic acid with CAS nr 120-18-3 was sourced from Alfa Aesar.

The octadecylamine CAS nr 214-30-1 was sourced from Alfa Aesar. The reaction has a molar ratio of naphthalene-2-sulfonic acid to octadecylamine 1:1.

The reaction was carried out for a few minutes at a temperature of 70° C. in alkylated naphthalene Na-Lube KR 008 oil (from King Industries Inc).

The first reaction product was then blended in equal amounts with the second reaction product, and mixed with extra Nalube oil.

The final preservative composition consisted of 66.8 wt. % Nalube oil, 27.5 wt. % PAO, 3.1 wt. % maleic anhydride-derived amide, and 2.6 wt. % sulfonic acid-derived amide.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 2. The five rollers showed mostly only one clear corrosion spot. Five rollers dipped in Na-Lube KR 008 oil showed all five corrosion. Five rollers dipped in the PAO oil showed all five signs of corrosion.

Example 5

First, maleic anhydride was reacted with an amine.

Octylamine (from Alfa Aesar CAS nr 111-86-4) was reacted with maleic anhydride (from Sigma Aldrich CAS nr 108-31-6) in a molar ratio of 1:1. This reaction was carried out in PAO 68 cSt (INEOS) for a few minutes. This PAO is a blend of PAO 46—Durasyn 168—and PAO 400—Durasyn 174—both PAO products were sourced from INEOS. The reaction has been run at a temperature of 70° C.

A second reaction was then carried out between naphtalene-2-sulfonic acid and octadecylamine. The naphthalene-2-sulfonic acid with CAS nr 120-18-3 was sourced from Alfa Aesar.

The octadecylamine CAS nr 214-30-1 was sourced from Alfa Aesar. The reaction has a molar ratio of naphthalene-2-sulfonic acid to octadecylamine 1:1. The reaction was carried out for a few minutes at a temperature of 70° C. in alkylated naphthalene Na-Lube KR 008 oil (from King Industries Inc).

The first reaction product was then blended in equal amounts with the second reaction product, and mixed with extra Nalube oil.

The final preservative composition consisted of 60.4 wt. % Nalube oil, 32.8 wt. % PAO, 3.6 wt. % maleic anhydride-derived amide, and 3.2 wt. % sulfonic acid-derived amide.

Figure 3:
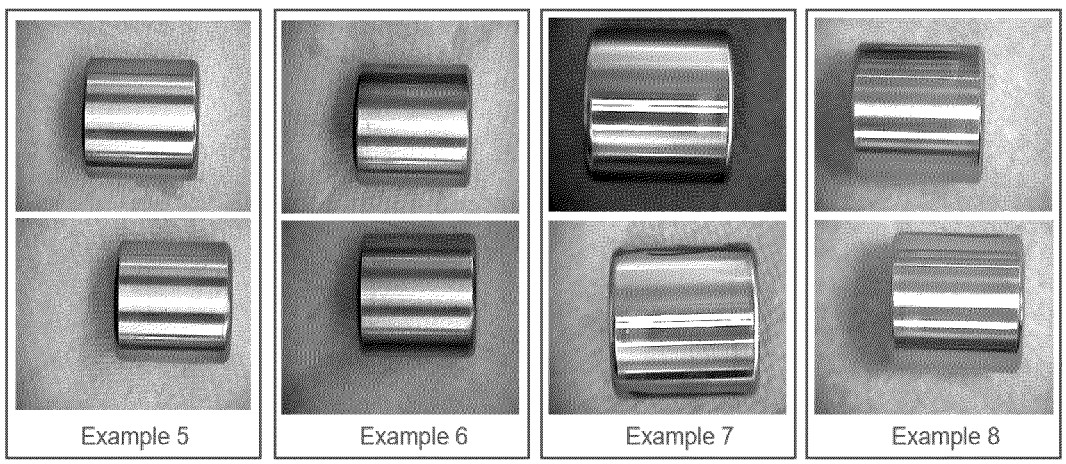
FIG. 3 shows 4 examples of roller pairs.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 3. The five rollers show few corrosion spots. Five rollers dipped in Na-Lube KR 008 oil showed all five corrosion. Five rollers dipped in the PAO oil showed all five signs of corrosion.

Example 6

First, succinic anhydride was reacted with an amine.

Dodecylamine (from Alfa Aesar CAS nr 124-22-1) was reacted with succinic anhydride (from Alfa Aesar CAS nr 108-30-5) in a molar ratio of 1:1.

This reaction was carried out in alkylated naphthalene Na-Lube KR 008 oil (from King Industries Inc) for a few minutes. The reaction was carried out at a temperature of 70° C.

A second reaction was then carried out between naphthalene-2-sulfonic acid and octadecylamine. The naphthalene-2-sulfonic acid with CAS nr 120-18-3 were sourced from Alfa Aesar. The octadecylamine CAS nr 214-30-1 was sourced from Alfa Aesar. The reaction has a molar ratio of naphthalene-2-sulfonic acid to octadecylamine 1:1. The reaction was carried out for a few minutes at a temperature of 70° C. in alkylated naphthalene Na-Lube KR 008 oil (from King Industries Inc).

The first reaction product was then blended in equal amounts with the second reaction product, and mixed with extra Nalube oil.

The final preservative composition consisted of 95.3 wt. % Nalube oil, 2.5 wt. % maleic anhydride-derived amide and 2.2 wt. % sulfonic acid-derived amide.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 3. The five rollers showed few corrosion spots. Five rollers dipped in Na-Lube KR 008 oil showed all five corrosion. Five rollers dipped in the PAO oil showed all five signs of corrosion.

Example 7

First, maleic anhydride was reacted with an amine.

Octadecylamine (from Alfa Aesar CAS nr 214-30-1) was reacted with maleic anhydride (from Sigma Aldrich CAS nr 108-31-6) in a molar ratio of 2:1 (amine:maleic anhydride).

This reaction was carried out in alkylated naphthalene Na-Lube KR 008 oil (from King Industries Inc) for a few minutes. The reaction was carried out at a temperature of 70° C.

This reaction product was then blended with extra Nalube oil.

The final preservative composition consisted of 92.5 wt. % Nalube oil, and 7.5 wt. % maleic anhydride-derived amide.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 3. The five rollers showed no corrosion. Five rollers dipped in Na-Lube KR 008 oil showed all five signs of corrosion.

Example 8

First, maleic anhydride was reacted with an amine.

Octadecylamine (from Alfa Aesar CAS nr 214-30-1) was reacted with maleic anhydride (from Sigma Aldrich CAS nr 108-31-6) in molar ratio of 2:1 (amine:maleic anhydride).

This reaction was carried out in alkylated naphthalene Na-Lube KR 008 oil (from King Industries Inc) for a few minutes. The reaction was carried out at a temperature of 70° C.

This reaction product was then blended with extra Nalube oil.

The final preservative composition consisted of 94.7 wt. % Nalube oil, and 5.3 wt. % maleic anhydride-derived amide.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 3. The five rollers did no show corrosion spots. Five rollers dipped in Na-Lube KR 008 oil showed all five signs of corrosion.

Example 9

First, maleic anhydride was reacted with an amine.

Octadecylamine (from Alfa Aesar CAS nr 214-30-1) was reacted with maleic anhydride (from Sigma Aldrich CAS nr 108-31-6) in a molar ratio of 2:1 (amine:maleic anhydride).

This reaction was carried out in alkylated naphthalene Na-Lube KR 008 oil (from King Industries Inc) for a few minutes. The reaction was carried out at a temperature of 70° C.

A second reaction was then carried out between naphthalene-2-sulfonic acid and octadecylamine. The naphthalene-2-sulfonic acid with CAS nr 120-18-3 was sourced from Alfa Aesar.

The octadecylamine CAS nr 214-30-1 was sourced from Alfa Aesar. The reaction had a molar ratio of naphthalene-2-sulfonic acid to octadecylamine 1:1.

The reaction was carried out for a few minutes at a temperature of 70° C. in alkylated naphthalene Na-Lube KR 008 oil (from King Industries Inc).

Both reaction products were then blended with a mixture of Nalube and lutensol AO3.

The mixture so obtained was then heat treated again to 90° C.

The final preservative composition consisted of 60 wt. % Nalube oil, 15 wt. % maleic anhydride-derived amide—amine, 15 wt. % sulfonic acid-derived amide and 10 wt. % lutensol A03.

Figure 4:
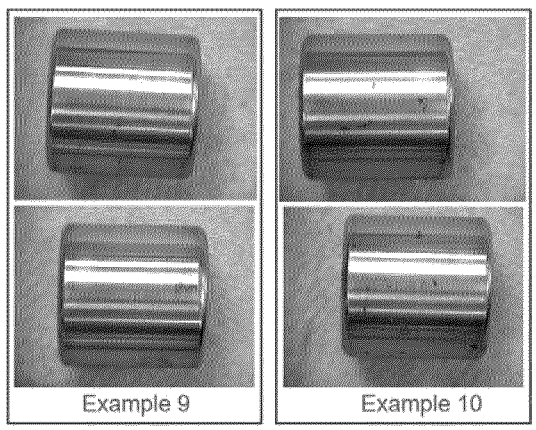
FIG. 4 shows 2 examples of roller pairs.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 4. The five rollers show a few corrosion spots. Five rollers dipped in Na-Lube KR 008 oil showed all five signs of corrosion.

Example 10

First, maleic anhydride was reacted with an amine.

Octadecylamine (from Alfa Aesar CAS nr 214-30-1) was reacted with maleic anhydride (from Sigma Aldrich CAS nr 108-31-6) in a molar ratio of 2:1 (amine:maleic anhydride).

This reaction was carried out in alkylated naphthalene Na-Lube KR 008 oil (from King Industries Inc) for a few minutes. The reaction was carried out at a temperature of C 70° C.

A second reaction was then carried out between naphthalene-2-sulfonic acid and octadecylamine. The naphthalene-2-sulfonic acid with CAS nr 120-18-3 was sourced from Alfa Aesar.

The octadecylamine CAS nr 214-30-1 was sourced from Alfa Aesar. The reaction had a molar ratio of naphthalene-2-sulfonic acid to octadecylamine 1:1. The reaction was carried out for a few minutes at a temperature 70° C. in alkylated naphthalene Na-Lube KR 008 oil (from King Industries Inc).

Both reaction products were then blended with a mixture of Nalube and lutensol AO3. The mixture so obtained was heat treated again to 90° C.

The final preservative composition consisted of 55 wt. % Nalube oil, 15 wt. % maleic anhydride-derived amide, 15 wt. % sulfonic acid-derived amide and 15 wt. % lutensol A03.

Five rollers were then dipped into the final preservative. The dipped rollers then tested for 6 days according to the described cleaning method and the climate corrosion method IEC-60068-2-30-TEST-DB-Variante 1. Two rollers so obtained are shown in FIG. 4. The five rollers show a few corrosion spots. Five rollers dipped in Na-Lube KR 008 oil showed all five signs corrosion.

The results of Examples 1-10 as shown FIGS. 2-4 clearly show that in accordance with the present invention a very attractive new class of preservatives is provided that effectively prevent and/or reduce corrosion on bearing rollers.

The invention claimed is:

1. A preservative composition to prevent and/or reduce corrosion on a metal surface comprising an anhydride-derived amide and an oil and/or a solvent, wherein the anhydride-derived amide is present in an amount in the range of from 0.01-50 wt %, based on the total weight of the preservative composition, wherein the anhydride-derived amide is a maleic anhydride-derived amide having the following general formula (I):

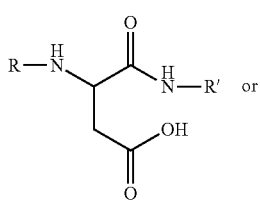
(I)

or the anhydride-derived amide is a maleic anhydride-derived ammonium salt having the following general formulas (IV) or (V):

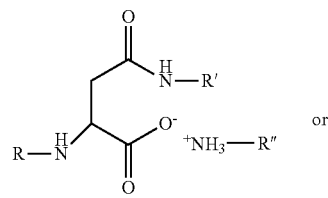
(IV)

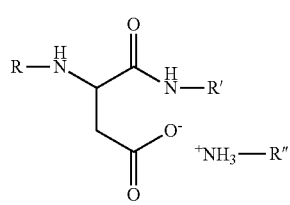
(V)

wherein in each of formulas (I), (IV) and (V), R and R' each independently represents a hydrocarbon group containing up to 28 carbon atoms.

2. The preservative composition according to claim 1, wherein the anhydride-derived amide is a maleic anhydride-derived amide having the following general formula (I):

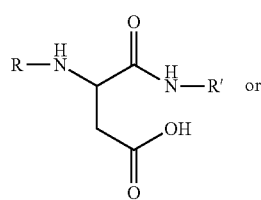
(I)

wherein R and R' each independently represents a hydrocarbon group containing up to 28 carbon atoms.

3. The preservative composition according to claim 1, wherein R and R' each independently represent a saturated unbranched alkyl group containing 8-18 carbon atoms.

4. The preservative composition according to claim 1, wherein the maleic anhydride-derived amide or the maleic anhydride-derived ammonium salt is obtained by reacting maleic acid with a fatty acid amine.

5. The preservative composition according to claim 4, wherein the fatty acid amine is unbranched and contains 8-18 carbon atoms.

6. The preservative composition according to claim 5, wherein the fatty acid amine is saturated.

7. The preservative composition according to claim 1, further comprising a sulfonate composition that is obtainable by a process in which an aromatic ring-containing sulfonic acid is reacted with an amine in the presence of an oil and/or a solvent at a temperature in the range of from 20-120° C., and wherein the molar ratio of the sulfonic acid (S) to the amide (A) is in the range of from 0.2-3 (S/A).

8. The preservative composition according to claim 7, wherein the sulfonate composition is obtainable by a process in which the aromatic ring-containing sulfonic acid is reacted with a fatty acid amine.

9. The preservative composition according to claim 7, wherein the aromatic ring-containing sulfonic acid is a naphthalene ring-containing sulfonic acid selected from the group consisting of naphthalene sulfonic acid, anthracene sulfonic acid and phenanthrene sulfonic acid.

10. The preservative composition according to claim 9, wherein the naphthalene ring-containing sulfonic acid is naphthalene sulfonic acid.

11. A preservative composition to prevent and/or reduce corrosion on a metal surface comprising an anhydride-derived amide and an oil and/or a solvent, wherein the anhydride-derived amide is present in an amount in the range of from 0.01-50 wt %, based on the total weight of the preservative composition, wherein the anhydride-derived amide is a maleic anhydride-derived amide having the following general formula (I):

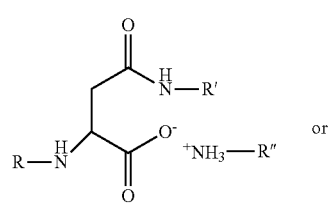
(I)

or the anhydride-derived amide is a maleic anhydride-derived ammonium salt having the following general formulas (IV) or (V):

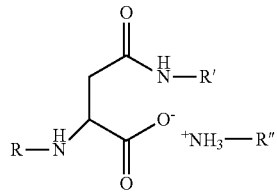
(IV)

or

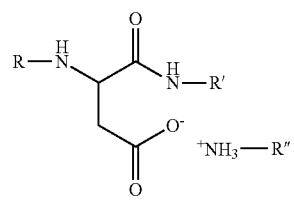
(V)

wherein in each of formulas (I), (IV) and (V), R and R' each independently represents a hydrocarbon group containing up to 28 carbon atoms, the preservative composition further comprising a sulfonate composition that is obtainable by a process in which an aromatic ring-containing sulfonic acid is reacted with an amine in the presence of an oil and/or a solvent at a temperature in the range of from 20-120° C., and wherein the molar ratio of the sulfonic acid (S) to the amide (A) is in the range of from 0.2-3 (S/A), wherein the sulfonate composition is a sulfonic acid-derived amide composition having the following general formula:

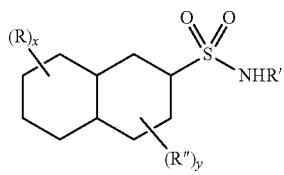

wherein R' represents a hydrocarbon group containing up to 30 carbon atoms, the hydrocarbon group R' also including a naphthalene ring, R and R" each independently represents a hydrocarbon group containing up to 28 carbon atoms or a hydroxyl group, and x is in the range of from 0-4 and y is in the range of 0-3.

12. A preservative composition to prevent and/or reduce corrosion on a metal surface comprising an anhydride-derived amide and an oil and/or a solvent, wherein the anhydride-derived amide is present in an amount in the range of from 0.01-50 wt %, based on the total weight of the preservative composition, wherein the anhydride-derived amide is a maleic anhydride-derived amide having the following general formula (I):

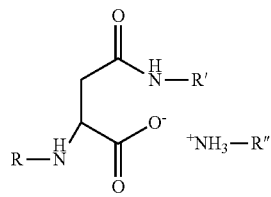
(I)

or

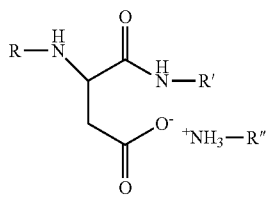
(II)

or the anhydride-derived amide is a maleic anhydride-derived ammonium salt having the following general formulas (IV) or (V):

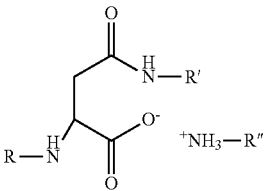
(IV)

or

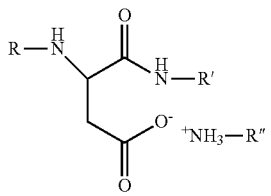
(V)

wherein in each of formulas (I), (IV) and (V), R and R' each independently represents a hydrocarbon group containing up to 28 carbon atoms, the preservative composition further comprising a sulfonate composition that is obtainable by a process in which an aromatic ring-containing sulfonic acid is reacted with an amine in the presence of an oil and/or a solvent at a temperature in the range of from 20-120° C., and wherein the molar ratio of the sulfonic acid (S) to the amide (A) is in the range of from 0.2-3 (S/A), wherein the sulfonate composition is a sulfonate ammonium salt composition having the following general formula:

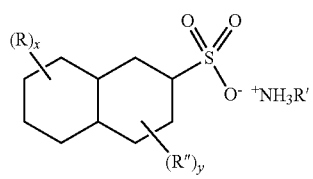

wherein R' represents a hydrocarbon group containing up to 30 carbon atoms, the hydrocarbon group R' also including a naphthalene ring, R and R" each independently represents a hydrocarbon group containing up to 28 carbon atoms or a hydroxyl group, and x is in the range of from 0-4 and y is in the range of 0-3.

13. The preservative composition according to claim 11, wherein R' represents a saturated and unbranched hydrocarbon group containing 10-22 carbon atoms.

14. The preservative composition according to claim 7, wherein the sulfonate composition is present in an amount in the range of from 0.01-30 wt. %, based on the total weight of the preservative composition.

15. The preservative composition according to claim 1, which in addition contains an emulsifier in an amount in the range of from 0.01-30 wt. %, based on the total weight of the preservative composition.

16. A metal article coated by the preservative composition of claim 1.

* * * * *